United States Patent [19]

Latini

[11] Patent Number: 5,356,385
[45] Date of Patent: Oct. 18, 1994

[54] HYPODERMIC NEEDLE SHEATH HOLDER

[75] Inventor: Claudio Latini, Rome, Italy

[73] Assignee: Kenneth T. O'Dell, Mt. Prospect, Ill.

[21] Appl. No.: 173,123

[22] Filed: Dec. 27, 1993

[30] Foreign Application Priority Data

Jan. 29, 1993 [IT] Italy .................... RM93A000050

[51] Int. Cl.$^5$ ................................. A61M 5/00
[52] U.S. Cl. ........................ 604/110; 206/366
[58] Field of Search .............. 604/110, 192, 263, 187;
206/365, 366, 364

[56] References Cited

U.S. PATENT DOCUMENTS 4,955,865  9/1990  Steiner et al. .................. 604/192
4,995,871  2/1991  Sasaki et al. .................. 206/366 X
5,069,667  12/1991  Freundlich et al. .................. 604/110

Primary Examiner—John D. Yasko
Attorney, Agent, or Firm—Richard W. Carpenter

[57] ABSTRACT

A hypodermic syringe needle sheath holder, designed to prevent accidental pricking by a needle. The device can be operated with one hand and includes a housing with a sheath gripping mechanism mounted under the housing upper wall. The mechanism comprises a plurality of gripper blades pivotally mounted for movement between gripping and release positions, actuating means normally biasing the blades to gripping position, and release means for overcoming the actuating means to permit the insertion and withdrawal of a sheath therefrom.

20 Claims, 1 Drawing Sheet

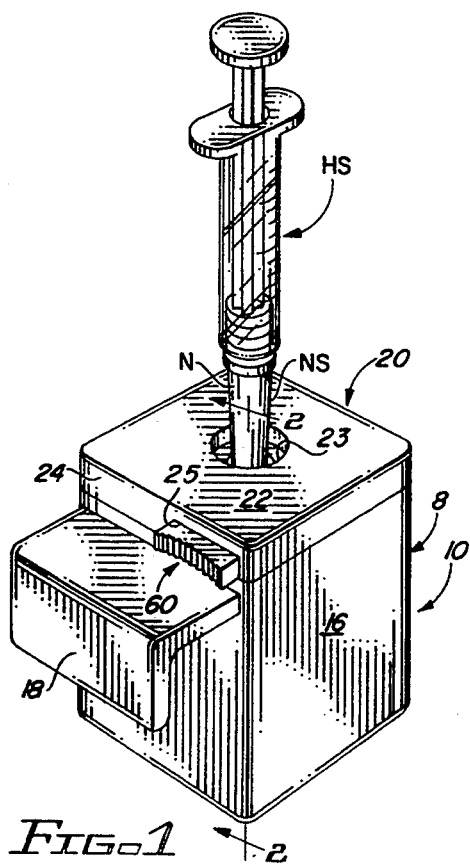
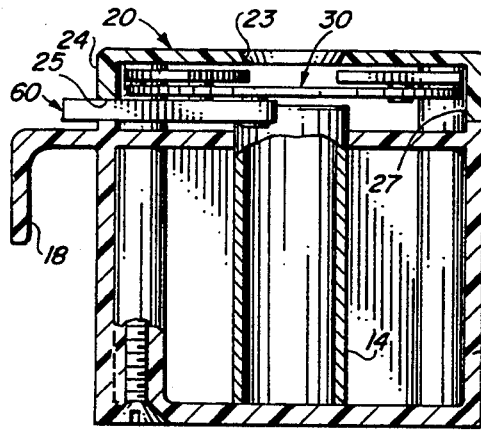
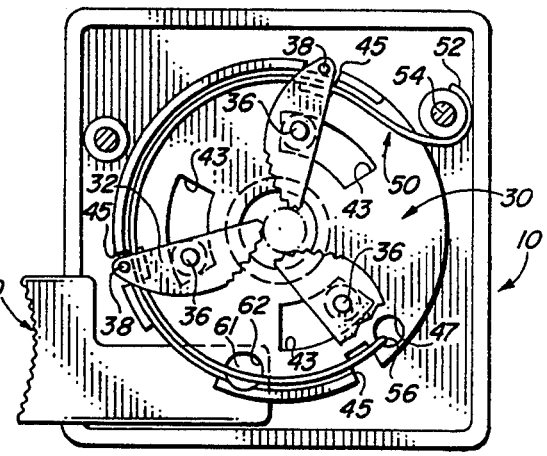
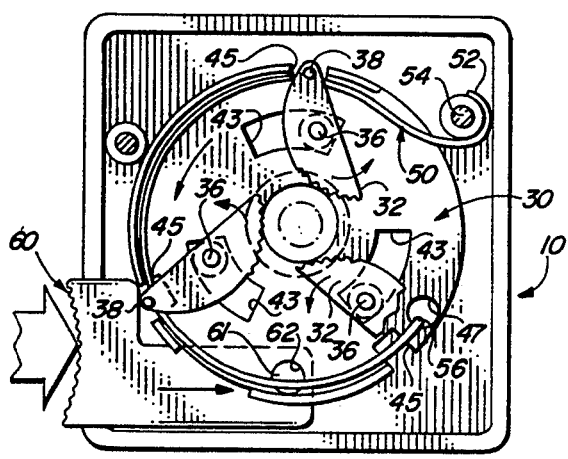
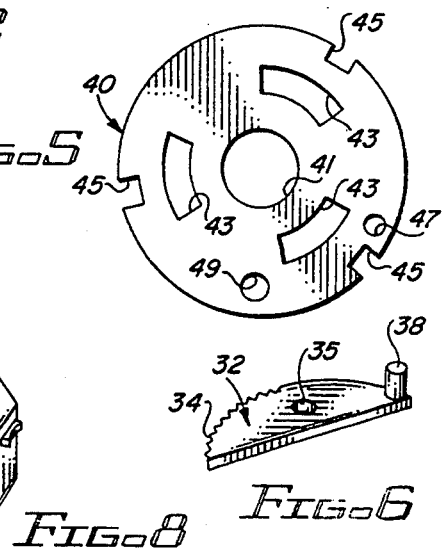
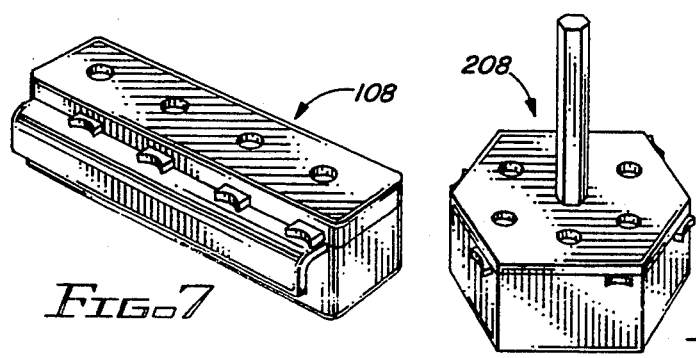

HYPODERMIC NEEDLE SHEATH HOLDER

BACKGROUND OF THE INVENTION

1. Field of the Invention

This invention relates to holders for hypodermic needle syringe sheaths, and more particularly to a holder designed to prevent accidental pricking of the finger of the user by an uncovered needle.

2. Description of the Background Art

A background art search directed to the subject matter of this invention conducted in the United States Patent and Trademark Office disclosed the following United States Letters Patent:

| | | | |
|---|---|---|---|
| Des. 325,438 | 4,742,910 | 4,830,319 | 4,890,734 |
| 4,938,354 | 4,955,865 | 4,995,871 | 5,013,299 |
| 5,024,666 | 5,067,949 | 5,242,426 | |

None of the patents uncovered in the search discloses a hypodermic syringe needle sheath holder operable by one hand and which includes a housing with a sheath gripping mechanism mounted under the housing upper wall and comprising a plurality of gripper blades pivotally mounted for movement between gripping and release positions, actuating means normally biasing the blades to gripping position, and release means for overcoming the actuating means to permit the insertion and withdrawal of a sheath therefrom.

SUMMARY OF THE INVENTION

It is a primary object of the invention to provide a sheath holder for a hypodermic syringe needle, or other type of medical needle, that can be easily operated by one hand and is designed to prevent accidental pricking of the hand of the user when inserting the needle into or removing it from a protective sheath.

Another object of the invention is the provision of a needle sheath holder including a housing, for temporarily receiving portions of a needle sheath; gripping means, for gripping the sheath while a needle is being inserted into or removed from the sheath; and release means, for counteracting the gripping means.

A more specific object of the invention is to provide a device of the type described which includes a housing with a sheath gripping mechanism mounted under the housing upper wall and comprising a plurality of gripper blades pivotally mounted for movement between gripping and release positions, actuating means normally biasing the blades to gripping position, and release means for overcoming the actuating means to permit the insertion and withdrawal of a sheath therefrom.

These and other objects of the invention will be apparent from an examination of the following description and drawings.

BRIEF DESCRIPTION OF THE DRAWINGS

FIG. 1 is a fragmentary isometric view of a hypodermic syringe sheath holder embodying features of the present invention;

FIG. 2 is a fragmentary vertical sectional view taken on line 2—2 of FIG. 1;

FIGS. 3 and 4 are bottom plan views of the underside of the housing cover shown in the previous views, and illustrate the gripper mechanism of the invention;

FIG. 5 is a plan view of the rotor plate illustrated in FIGS. 2-4;

FIG. 6 is an isometric view of one of the gripper blades illustrated in FIGS. 2-4; and FIGS. 7 and 8 are views similar to that of FIG. 1, but reduced in scale and illustrating modified forms of the invention.

It will be understood that, for purposes of clarity, certain elements may have been omitted from certain views where they are believed to be illustrated to better advantage in other views.

DESCRIPTION OF THE PREFERRED EMBODIMENT

There is little equipment available to hypodermic syringe operators for preventing accidental needle pricking, and such equipment as may be available is not very efficient nor safe.

For example extra thick rubber gloves, intended to protect the operator's hands, and rigid wall plastic container, for containing used injection syringes and needles, have been used. Also, plastic disks fitted around the needle cap opening have been used to try to protect the hand of a person holding a needle cap from being accidentally pricked.

Unfortunately, none of the above items have proven to be totally satisfactory for the purpose of avoiding accidental needle-pricking and consequent disease transmission resulting from the accidental pricking by a needle.

A very high percentage of accidents still occur, and infectious diseases are transmitted through the accidental pricking of operators using hypodermic syringes.

The present invention is intended to allow an operator to be protected from accidental needle pricking while efficiently and safely removing a needle from a sheath or reinserting it in the sheath.

Referring now to the drawings for a better understanding of the invention, as best seen in FIGS. 1 and 2, the invention comprises a holder with a housing, indicated generally at 8, for temporarily holding sheath NS while a needle N of a hypodermic syringe HS is being removed from or inserted into the sheath.

Housing 8 includes a hollow, generally cube-shaped body 10 and a cover 20 detachably secured to the top of the body.

Body 10 has a horizontal upper wall 12, with a circular central opening 13 extending therethrough, and an integral tube 14, depending from the upper wall in alignment with the upper wall opening, Body 10 also includes a side wall 16, depending from the outer periphery of the upper wall, and a finger grip 18, preferably generally L-shaped in cross-section, projecting outwardly from the side wall 16. The purpose of the finger grip is to accommodate the operation of the device by one hand, as described later herein.

Cover 20 includes an upper wall 22 with a circular central opening 23 extending therethrough in axial alignment with the body central opening 13 and tube 14.

Cover 20 also includes a side wall 24 depending from the outer periphery of the upper wall. Side wall 24 has extending therethrough an opening 25 for receiving an arm 60 of a gripper mechanism 30, as hereinafter described.

The heart of the invention resides in the gripper mechanism 30 most of which is positioned in the space or cavity 27 located between the cover upper wall 22 and the body upper wall 12.

Gripper mechanism 30 includes several, preferably three, relatively thin, generally crescent shaped, gripper blades 32, each having, at an inboard end thereof a serrated edge 34. The gripper blades also have extending therethrough central openings 35 for receipt of pivot pins 36 projecting downwardly from the underside of cover upper wall 20.

Thus, the gripper blades are mounted for rotational movement in a horizontal plane between a gripping position, when the blade serrated edges are close to the cover and body upper wall openings, and a release position, when the blade serrated edges are away from the cover and body upper wall openings.

At their outboard ends, gripper blades 32 have, extending downwardly therefrom, lugs or cleats 38 adapted to be received within complementary openings or notches 45 adjacent the outer periphery of a rotor plate 40, which is positioned in cavity 27 immediately below the gripper blades.

Rotor plate 40 is a relatively thin, flat, circular plate with a central opening 41, aligned with cover and body openings 23 and 13, and three slots 43 adapted to receive respective pivot pins 36.

Rotor plate 40 also has extending therethrough, near the outer periphery thereof, an opening 47, for receiving an end 56 of a spring 50, and an opening 49, for receiving a pin 62 projecting from a release arm 60.

Spring 50 is a circular, wire, torque spring that is mounted below rotor plate 40, with one end 52 secured to cover upper wall 20 at 54, and with the other end 56 extending through opening 47 of rotor plate 40.

Spring 50 normally biases rotor plate 40 in a clockwise direction, as seen in FIGS. 3 and 4, causing the gripper blades to rotate to the closed or gripping position of FIG. 3.

The rotor plate 40 can be rotated in the opposite (or counterclockwise direction) by means of a release arm 60 extending through cover side wall opening 25 into the cavity 27. The inboard end of arm 60 is pivotally connected to rotor plate 40 by a pivot pin 62 extending through opening 61 in the arm and through opening 49 in the rotor plate.

The operation of the device can be effected by one hand of the operator while a hypodermic syringe HS, containing a needle N with a cover or sheath NS.

To remove the needle from the sheath without touching either the needle or the sheath, the operator grasps the body, by placing one or more fingers under the body finger grip 18, and with another finger or thumb, pushes in the release arm 60.

This action causes the rotor plate to rotate in a clockwise position, as seen in FIG. 4, to pivot the gripper blades and move them to the open or release position away from the body and cover openings.

The operator can then insert the needle sheath into the housing until the sheath extends through both cover and body upper wall openings and part way down into body tube 14. At this time the operator releases the release arm, allowing the spring 50 to bias the rotor plate in the clockwise position to the gripping position, whereby the gripper blades engage and grasp the sheath to hold it in position while the operator withdraws the needle from the sheath.

After the needle has been used, the operator can reinsert the needle into the sheath, which is being held in the device, and can then withdraw the needle and sheath from the device by pushing the release arm again to move the gripper blades to the open or release position.

Thus, it should be appreciated that the invention provides a simple and safe device that minimizes the risk of infection to one using hypodermic or other types of medical needles that have to be removed from or inserted into protective sheaths.

Turning now to FIGS. 7 and 8, it will be seen that slightly modified forms of the invention are shown. In each of these embodiments the housings are adapted to enclose a plurality of gripper mechanisms (not shown) of the type previously described.

The device 108 illustrated in FIG. 7 has a housing 110 which is elongated, with several gripping stations arranged in a row, whereas the device 208 illustrated in FIG. 8 has a housing 210 which is octagonal, with the gripping stations arranged in a circular pattern around the housing. In each embodiment elements corresponding to elements of the previously described embodiment are identified by corresponding numerals.

The operation of the gripping mechanisms of all of the embodiments of the invention is the same as described in connection with the first embodiment, except that the embodiments of FIGS. 7 and 8 allow the insertion and retaining of several needle sheaths at the same time.

What is claimed is:

1. A device for holding a hypodermic syringe needle sheath to prevent human contact with a needle during its insertion into and removal from the sheath, said device comprising:
   (a) a housing including a body and a cover;
   (b) said cover having an upper wall with an opening extending therethrough;
   (c) said body having an upper wall, with an opening extending therethrough, and having an integral tube extending vertically downward therefrom, in axial alignment with both of said openings and adapted to receive a portion of a hypodermic needle sheath that may be inserted through said openings;
   (d) a sheath gripping mechanism located in said housing between said cover and body upper walls and including:
   (i) a plurality of gripper blades, with serrated edges, mounted for pivotal movement in a horizontal plane under said cover opening between a sheath gripping position, wherein said blades are close to each other, and a release position, wherein said blades are away from each other;
   (ii) spring means normally biasing said gripper blades toward said gripping position;
   (iii) release means for temporarily overcoming biasing action of said spring means to permit the insertion of a needle sheath into said housing and the withdrawal therefrom;
   (d) handle means on said body for cooperation with said release means to allow use of said release means with one hand.

2. A device for holding a hypodermic syringe needle sheath to prevent human contact with a needle during its insertion into and removal from the sheath, said device comprising:
   (a) a housing including a body and a cover;
   (b) said cover having an upper wall with an opening extending therethrough;
   (b) said body having an upper wall with an opening extending therethrough in axial alignment with both of said openings and adapted to receive a portion of a hypodermic needle sheath that may be inserted through said openings;

(c) a sheath gripping mechanism located in said housing between said cover and body upper walls and including:

(i) a plurality of gripper blades, with serrated edges, mounted for pivotal movement in a horizontal plane under said cover opening between a sheath gripping position, wherein said blades are close to each other, and a release position, wherein said blades are away from each other;

(ii) spring means normally biasing said gripper blades toward said gripping position;

(iii) release means for temporarily overcoming biasing action of said spring means to permit the insertion of a needle sheath into said housing and the withdrawal therefrom.

3. A device for holding a hypodermic syringe needle sheath to prevent human contact with a needle during its insertion into and removal from the sheath, said device comprising:

(a) a housing having an upper wall with an opening extending therethrough adapted to receive a portion of a hypodermic needle sheath that may be inserted through said openings;

(b) a sheath gripping mechanism located in said housing under said upper wall and including:

(i) a plurality of gripper blades mounted for pivotal movement in a horizontal plane under = said cover opening between a sheath gripping position, wherein said blades are close to each other, and a release position, wherein said blades are away from each other;

(ii) spring means normally biasing said gripper blades toward said gripping position;

(iii) release means for temporarily overcoming biasing action of said spring means to permit the insertion of a needle sheath into said housing and the withdrawal therefrom.

4. A device according to claim 3, wherein said housing includes a body and a cover, detachably secured to said body and including said upper wall, and wherein said body also has an upper wall with an opening extending therethrough, in axial alignment with said cover upper wall opening and adapted to receive a portion of a hypodermic needle sheath that may be inserted into said openings.

5. A device according to claim 2, wherein said body includes an integral tube extending vertically downward from said body upper wall, in axial alignment with both of said openings, and adapted to receive a portion of a hypodermic needle sheath that may be inserted through said openings.

6. A device according to claim 4, wherein said body includes an integral tube extending vertically downward from said body upper wall, in axial alignment with both of said openings, and adapted to receive a portion of a hypodermic needle sheath that may be inserted through said openings.

7. A device according to claim 1, wherein said sheath gripping mechanism includes actuating means, to bias said gripper blades into said gripping position, and release means to counteract said actuating means and move said gripper blades into said release position.

8. A device according to claim 2, wherein said sheath gripping mechanism includes actuating means, to bias said gripper blades into said gripping position, and release means to counteract said actuating means and move said gripper blades into said release position.

9. A device according to claim 3, wherein said sheath gripping mechanism includes actuating means, to bias said gripper blades into said gripping position, and release means to counteract said actuating means and move said gripper blades into said release position.

10. A device according to claim 7, wherein said actuating means includes a relatively thin, flat, round, rotor plate, mounted for rotational movement in a horizontal plane, having a plurality of openings adapted to receive portions of respective of said gripper blades, and a spring mounted in said housing in engagement with said rotor plate and normally operable to rotate said plate and move said gripper blades to the gripping position.

11. A device according to claim 8, wherein said actuating means includes a relatively thin, flat, round, rotor plate, mounted for rotational movement in a horizontal plane, having a plurality of openings adapted to receive portions of respective of said gripper blades, and a spring mounted in said housing in engagement with said rotor plate and normally operable to rotate said plate and move said gripper blades to the gripping position.

12. A device according to claim 9, wherein said actuating means includes a relatively thin, flat, round, rotor plate, mounted for rotational movement in a horizontal plane, having a plurality of openings adapted to receive portions of respective of said gripper blades, and a spring mounted in said housing in engagement with said rotor plate and normally operable to rotate said plate and move said gripper blades to the gripping position.

13. A device according to claim 7, wherein said release means includes an arm extending into said housing in engagement with said rotor plate and operable, when pushed manually from outside the housing to rotate said plate and move said gripper blades to the release position.

14. A device according to claim 8, wherein said release means includes an arm extending into said housing in engagement with said rotor plate and operable, when pushed manually from outside the housing to rotate said plate and move said gripper blades to the release position.

15. A device according to claim 9, wherein said release means includes an arm extending into said housing in engagement with said rotor plate and operable, when pushed manually from outside the housing to rotate said plate and move said gripper blades to the release position.

16. A device according to claim 3, wherein said housing includes a plurality of separate sheath gripping mechanisms spaced from each other and operable independently of each other.

17. A device according to claim 16, wherein said separate sheath gripping mechanisms are arranged in a row.

18. A device according to claim 16, wherein said separate gripping mechanisms are arranged in a circle.

19. A device according to claim 3, and including handle means on said housing for cooperation with said release means to allow the use of said release means with one hand.

20. A device according to claim 19, wherein said handle means includes a horizontal flange extending outwardly from said housing, adjacent an arm of said release means, and a vertical flange extending vertically downward from said horizontal flange whereby an operator can insert at least one finger behind said vertical flange and push said release means arm with another at the same time.

* * * * *